United States Patent
Hodge

(10) Patent No.: US 11,948,218 B2
(45) Date of Patent: Apr. 2, 2024

(54) SYSTEM AND METHOD FOR SECURELY DISPENSING MEDICATION

(71) Applicant: **Global Tel*Link Corporation**, Reston, VA (US)

(72) Inventor: Stephen L Hodge, Aubrey, TX (US)

(73) Assignee: **Global Tel*Link Corporation**, Reston, VA (US)

(*) Notice: Subject to any disclaimer, the term of this patent is extended or adjusted under 35 U.S.C. 154(b) by 0 days.

(21) Appl. No.: 17/228,195

(22) Filed: Apr. 12, 2021

(65) Prior Publication Data
US 2021/0304340 A1    Sep. 30, 2021

Related U.S. Application Data

(63) Continuation of application No. 15/139,015, filed on Apr. 26, 2016, now Pat. No. 10,977,753.

(51) Int. Cl.
  *G06Q 50/26* (2012.01)
  *G16H 20/13* (2018.01)
  *G16H 40/67* (2018.01)

(52) U.S. Cl.
  CPC ............. *G06Q 50/26* (2013.01); *G16H 20/13* (2018.01); *G16H 40/67* (2018.01)

(58) Field of Classification Search
  CPC ......... G16H 20/13; G16H 40/67; G06Q 50/26
  USPC ....................................................... 705/2–3
  See application file for complete search history.

(56) References Cited

U.S. PATENT DOCUMENTS

| 7,037,267 | B1 |  | 5/2006 | Lipson et al. |
| 7,278,028 | B1 | * | 10/2007 | Hingoranee ........... G07C 9/257 |
|  |  |  |  | 713/193 |
| 7,813,939 | B2 | * | 10/2010 | Clements ............... G16H 10/60 |
|  |  |  |  | 600/300 |
| 2005/0216310 | A1 |  | 9/2005 | Clements et al. |
| 2006/0097000 | A1 | * | 5/2006 | Gumpert ............... A61J 7/0481 |
|  |  |  |  | 221/92 |

(Continued)

OTHER PUBLICATIONS

International Search Report and Written Opinion directed to related International Patent Application No. PCT/US2017/029398, dated Jul. 26, 2017; 12 pages.

(Continued)

*Primary Examiner* — Michael Tomaszewski
(74) *Attorney, Agent, or Firm* — Sterne, Kessler, Goldstein & Fox P.L.L.C.

(57) ABSTRACT

A system and method for securely dispensing medication are described herein. The system includes a telemedicine center that communicates with medical assistant station and a medication distribution station located at a correctional facility and a physician center remote to the correctional facility. The medical assistant station transmits a request for medication to the telemedicine center. The telemedicine center verifies an identity of the medical assistant requesting the medication and transmits the request to the physician center. When the telemedicine center receives a confirmation to dispense medicine from the physician center, an identity of the physician transmitting the confirmation is verified. The telemedicine center then verifies an identity of an inmate to receive the medication, by way of the medication distribution station, and allows the medication distribution station to dispense the medication.

20 Claims, 9 Drawing Sheets

(56) References Cited

U.S. PATENT DOCUMENTS

| | | |
|---|---|---|
| 2006/0129273 A1 | 6/2006 | Kirsch et al. |
| 2006/0271400 A1 | 11/2006 | Clements et al. |
| 2007/0118389 A1 | 5/2007 | Shipon |
| 2007/0162309 A1* | 7/2007 | Denny ................. G06Q 20/203 705/2 |
| 2007/0260491 A1* | 11/2007 | Palmer .................. G16H 40/67 705/3 |
| 2009/0083066 A1 | 3/2009 | Bailey et al. |
| 2011/0202174 A1 | 8/2011 | Bogash et al. |
| 2012/0029303 A1 | 2/2012 | Shaya |
| 2012/0278228 A1 | 11/2012 | Rubinstein |
| 2013/0060576 A1 | 3/2013 | Hamm et al. |
| 2015/0294079 A1 | 10/2015 | Bergougnan |
| 2015/0310183 A1 | 10/2015 | Madhavan et al. |
| 2016/0055307 A1 | 2/2016 | Macoviak et al. |
| 2017/0199984 A1* | 7/2017 | Lohman ................. G16H 10/20 |
| 2017/0308983 A1 | 10/2017 | Hodge |
| 2017/0323070 A1 | 11/2017 | Hodge |
| 2021/0035400 A1* | 2/2021 | Flynn ..................... G07F 11/54 |

OTHER PUBLICATIONS

International Search Report and Written Opinion directed to International Patent Application No. PCT/US2017/031731, dated Aug. 2, 2017; 17 pages.

* cited by examiner

SYSTEM AND METHOD FOR SECURELY DISPENSING MEDICATION

CROSS-REFERENCE TO RELATED APPLICATIONS

This application is a continuation of U.S. patent application Ser. No. 15/139,015 filed on Apr. 26, 2016, which is incorporated by reference herein in its entirety.

BACKGROUND

Field

The disclosure relates to a telemedicine system that facilitates a secure tracking of medicine from time of ordering to dispensing of the medicine at a medicine dispenser.

Background

Traditionally, a correctional facility uses a remote medical doctor (M.D.) to perform check-ups and prescribe prescriptions to an inmate. The check-ups are usually performed by voice or video communication systems between the M.D. and the inmate. At the correctional facility, a local medical assistant assists with the check-up by performing tasks such as arranging the meeting and room, taking patient vitals, and administering medications such as prescriptions to the inmate. Because local medical assistants are physically at the correctional facility and are in close communication with inmates, local medical assistants may be unduly influenced by inmates in dispensing medication.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 1:
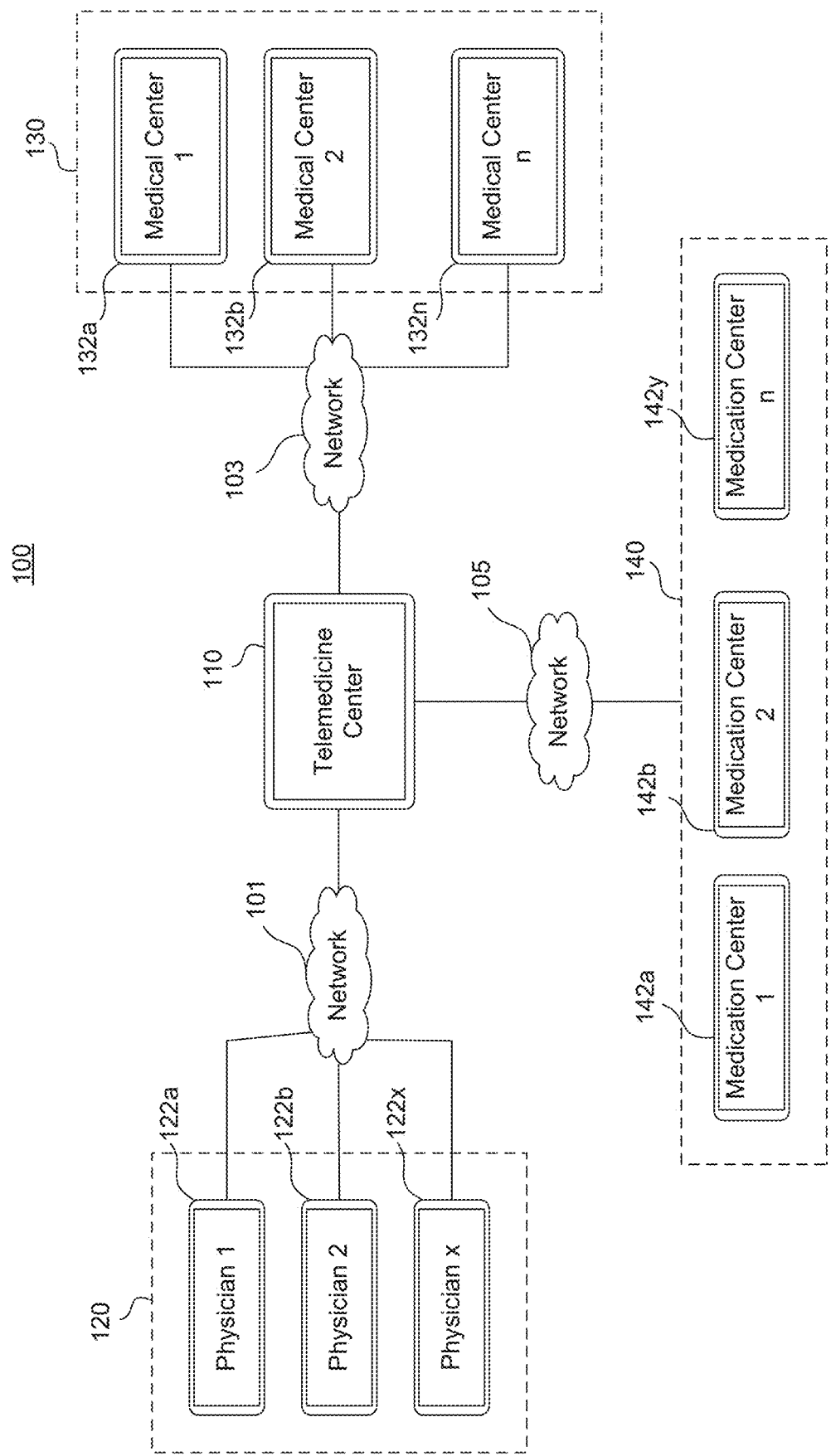
FIG. 1 illustrates a block diagram of a telemedicine system, according to exemplary embodiments of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. Further, any of the implementation variations may be carried out by a general purpose computer, as described below.

For purposes of this discussion, any reference to the term "module" shall be understood to include at least one of software, firmware, and hardware (such as one or more circuit, microchip, or device, or any combination thereof), and any combination thereof. In addition, it will be understood that each module may include one, or more than one, component within an actual device, and each component that forms a part of the described module may function either cooperatively or independently of any other component forming a part of the module. Conversely, multiple modules described herein may represent a single component within an actual device. Further, components within a module may be in a single device or distributed among multiple devices in a wired or wireless manner.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

Overview

In a correctional facility setting, medical doctors (M.D.s) are not typically present at a correctional facility. Instead, M.D.s provide medical check-ups through remote voice or video conferences involving inmates. To facilitate this, correctional facilities have medical rooms where an inmate is treated, similar to hospital, as a medical patient. The M.D.s may talk with and/or see the inmates to determine any symptoms and determine which disease or condition applies to the inmate. M.D.s may follow up on pre-existing conditions and diagnose new conditions. Treatment of the conditions may range anywhere from simple exercise or daily routine changes to the prescribing or renewing of medication. When a medication is prescribed, the M.D.s write up the prescription and send the prescription to a pharmacy for preparation of the medication.

To assist in hands-on procedures at correctional facilities, local medical assistants, such as nurse assistants, medical technicians, or registered nurses, are typically employed. Similar to medical assistants outside of correctional facilities, local medical assistants are stationed at the correctional facility to assist M.D.s in performing check-ups such as obtaining and recording situations surrounding a medical condition, and obtaining inmate vital signs, and/or following up on previous treatments or conditions. When medications are prescribed by M.D.s, local medical assistants additionally assist in distributing medications to an appropriate dispenser for an inmate to retrieve the medication and/or in administering medications to inmates.

Medications are dispensed at correctional facilities to treat both physical and mental illnesses such as infections, pain, and depression, as well as help prevent the spread of diseases. However, inmates that have access to such medications may use them improperly, such as by selling, trading to gain favors with other inmates, improperly administering the medications, facilitating addictions. This makes medications in a correctional facility a desired commodity. To obtain medications, inmates may attempt to unduly influence local medical assistants by way of manipulation, falsehoods, and/or duress.

In light of the above, the present disclosure provides a system and method for securely distributing and dispensing a medication such that local medical assistants do not have the option of obtaining medication for an inmate without a series of security measures first being performed.

Telemedicine System

FIG. 1 illustrates a block diagram of a telemedicine system 100, according to exemplary embodiments of the present disclosure. The telemedicine system 100 includes a telemedicine center 110 configured to communicate with a variety of devises over a variety of different communication networks. In particular, the telemedicine center 110 is configured with a physician center 120, a medical center 130, and a medication center 140. As will be further explained below, the telemedicine center 110 receives and transmits medical data, identification data, and scheduling data from/to the physician center 120, the medical center 130, and the medication center 140. To communicate with the physician center 120, the telemedicine center 110 interfaces with a network 101. The network 101 may be any one or more of a public switched telephone network (PSTN), a wide area network (WAN), or the Internet. To communicate with the medical center 130, the telemedicine center 110 interfaces with a network 103. The network 103 may be any one or more of a PSTN, a local area network (LAN), a WAN, or the internet. To communicate with the medication center 140, the telemedicine center 110 interfaces with a network 105. The network 105 may be any one or more of a public switched telephone network (PSTN), a WAN, or the Internet.

The physician center 120 is a location remote to a correctional facility that includes a medical doctor, physician assistant, nurse practitioner etc. The physician center 120 may be configured to include any number of physician devices 122a-122x for communicating with the telemedicine center 110. Each of the physician devices 122a-122x are configured to transmit medical data such as a request for medication, patient data, billing data, etc. Each of the physician devices 122a-122x may include one or more devices such as a computer, a tablet, a facsimile machine, etc. Further, the physician devices 122a-122x can be located at one location or any number of locations. For example, physician device 122a may be a computer located in Washington and physician device 122b may be a fax machine located in Missouri. Further examples and explanations of the physician devices 122a-122x will be in reference to the physician center 120.

The medical center 130 is a medical area provided at a correctional facility. The medical center 130 may include any number of medical centers 132a-132n. The medical centers 132a-132n may be located at one correction facility location or any number of correctional facilities. Each of the medical centers 132a-132n is configured to receive medical data, facilitate distribution of medication, and may perform identity verification of inmates and local medical assistants. Further examples and explanations of the medical centers 132a-132n will be in reference to the medical center 130. As will be explained in further detail below, the medical center 130 includes station(s) and dispenser(s) for distributing and dispensing medication.

The medication center 140 is a medication preparation center such as a pharmacy that prepares medication for distribution at a correctional facility. The medication center 140 may include any number of medication centers 142a-142y. The medication centers 142a-142y are located at locations remote to correction facilities. However, the telemedicine system 100 may also include local medication centers too. Each of the medication centers 142a-142y is configured to receive and transmit medical data, prepare medication for a correction facility, and distribute the prepared medication to correctional facilities. For example, medication center 1 142a may receive a request for medication from the telemedicine center 110, the medication is then prepared and packaged according to requirements set by a correctional facility to which the medication will be sent, and the medication is delivered to the correctional facility. Further examples and explanations of the medication centers 142a-142y will be in reference to the medication center 140.

Telemedicine Center

Figure 2:
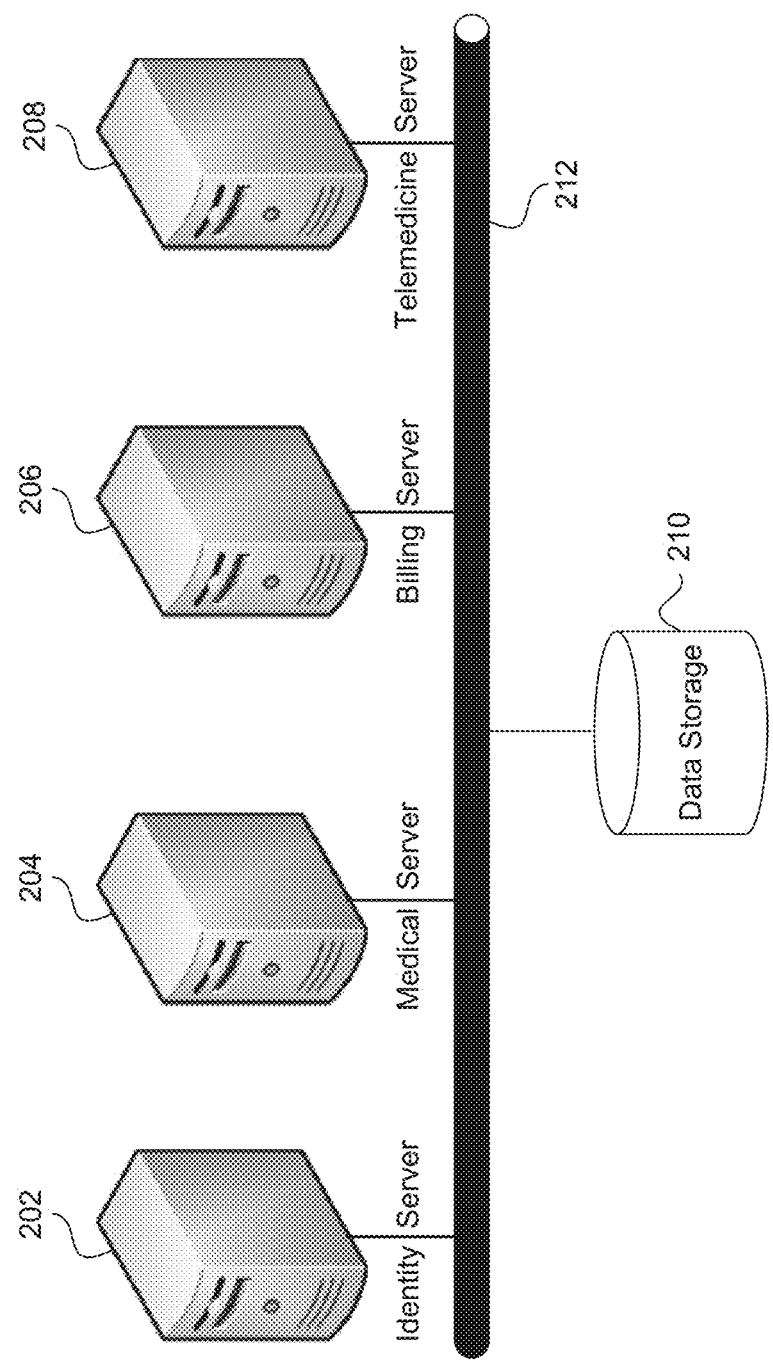
FIG. 2 illustrates a block diagram of a telemedicine center, according to exemplary embodiments of the present disclosure.

FIG. 2 illustrates a block diagram of a telemedicine center 200, according to exemplary embodiments of the present disclosure. The telemedicine center 200 may be an exemplary embodiment of the telemedicine center 110 of FIG. 1. The telemedicine center 200 includes an identity server 202, a medical server 204, a billing server 206, a telemedicine server 208, and data storage 210, that are all connected to each other via a network bus 212.

Each of the servers 202-208 can be constructed as individual physical hardware devices, or as virtual servers. The number of physical hardware machines can be scaled to match the number of simultaneous user connections desired to be supported in an telemedicine system such as the telemedicine system 100.

The identity server 202 consists of any number of servers, and is configured to store and organize identity data. The identity data includes data relating to physicians, inmates, and local medical assistants. The identity data includes such data as names, biometric data, and contact data of physicians, inmates, and local medical assistants allowed to access the telemedicine system. In an embodiment, the identity data also includes data related to the physician devices 122a-122x such as make and model of the devices and contact information, and/or data related to equipment from a correctional facility used to connect to the telemedicine system.

The medical server 204 also consists of any number of servers, and is configured to securely receive, organize, and transmit medical data. In essence, the medical server 204 is configured to receive medical data such as a request for medication data, medication fulfillment data, check-up data, medical questionnaires, etc., and to securely store the data. The medical server 204 can be configured to organize the medical data such that when the medical data is received it is tagged and linked to a corresponding physician, inmate, and/or local medical assistant, to facilitate searching the medical data. The medical server 204 is also configured to share some or all of the stored medical data within the telemedicine center and also with personnel such as physicians or local medical assistants, based on authorization. For example, a local medical assistant may only have access to a list of available prescriptions for an inmate while another local medical assistant or a physician may have access to all medical data of the same inmate.

The billing server 206 can consist of any number of servers, and is configured to securely receive, organize, and transmit billing and accounting data. In detail, the billing server 206 stores data relating to billing for an inmate. The billing data may include responsible billing parties or historical costs of medications. When the billing data is received, the received data is tagged and linked to a corresponding physician, inmate, and/or local medical assistant to facilitate searching the billing data. Similar to the medical server 204, the billing server 206 is also configured to share some or all of the stored data within the telemedicine center and also with personnel such as physicians or local medical assistants, based on authorization.

The telemedicine server 208 consists of any number of servers, and is configured to schedule and track the distribution of medications within the telemedicine system 100.

The telemedicine server 208 communicates with the physician center 120, the medical center 130 or the medication center 140 to schedule and coordinate distribution of a medication. For example, the telemedicine server 208 communicates with the physician center 120 to determine whether to distribute medication to a particular inmate. As another example, the telemedicine server 208 communicates with the medication center 140 to schedule when to distribute medication. As a further example, the telemedicine server 208 provides instructions to the medication center 140 to dispense medication.

To facilitate the scheduling of medication distribution, the telemedicine server 208 communicates with the identity server 202, the medical server 204, and the billing server 206. The telemedicine server 208 retrieves data gathered and stored by these servers and uses the data for such actions as validating an identity of a person making a request for medication and generating a schedule to distribute the medication. For example, after a request for medication has been received from the medication center 140, the telemedicine server 208 can confirm an identity of a local medical assist that submitted the request based on a comparison of identity verification data received with the request for medication with identity data stored on the identity server 202. To schedule the distribution of medication, the telemedicine server 204 can retrieve medication data stored by the medical server 204 to determine when to distribute medication, to provide an example.

While each of the servers 202-208 may be configured to store data on respective local storage devices, the data storage 210 is configured to store all the data that the servers 202-208 can store. In other words the data storage 210 can be either a primary storage or a back-up storage for the servers 202-208. Further, because the data stored on the data storage 210 may consume significant amounts of storage space, the data storage 210 may include a Network Attached Storage (NAS) device, which may be configured as a mass storage device. In order to reduce an amount of the data storage 210 preferably includes a backup routine to transfer data to permanent storage devices, such as archival permanent storage or optical disks, after a predetermined time has elapsed since the initial recording of that data. The storage device 210 is connected to identity server 202, the medical server 204, the billing server 206, and the telemedicine server 208 by way of the network bus 212.

Figure 3:
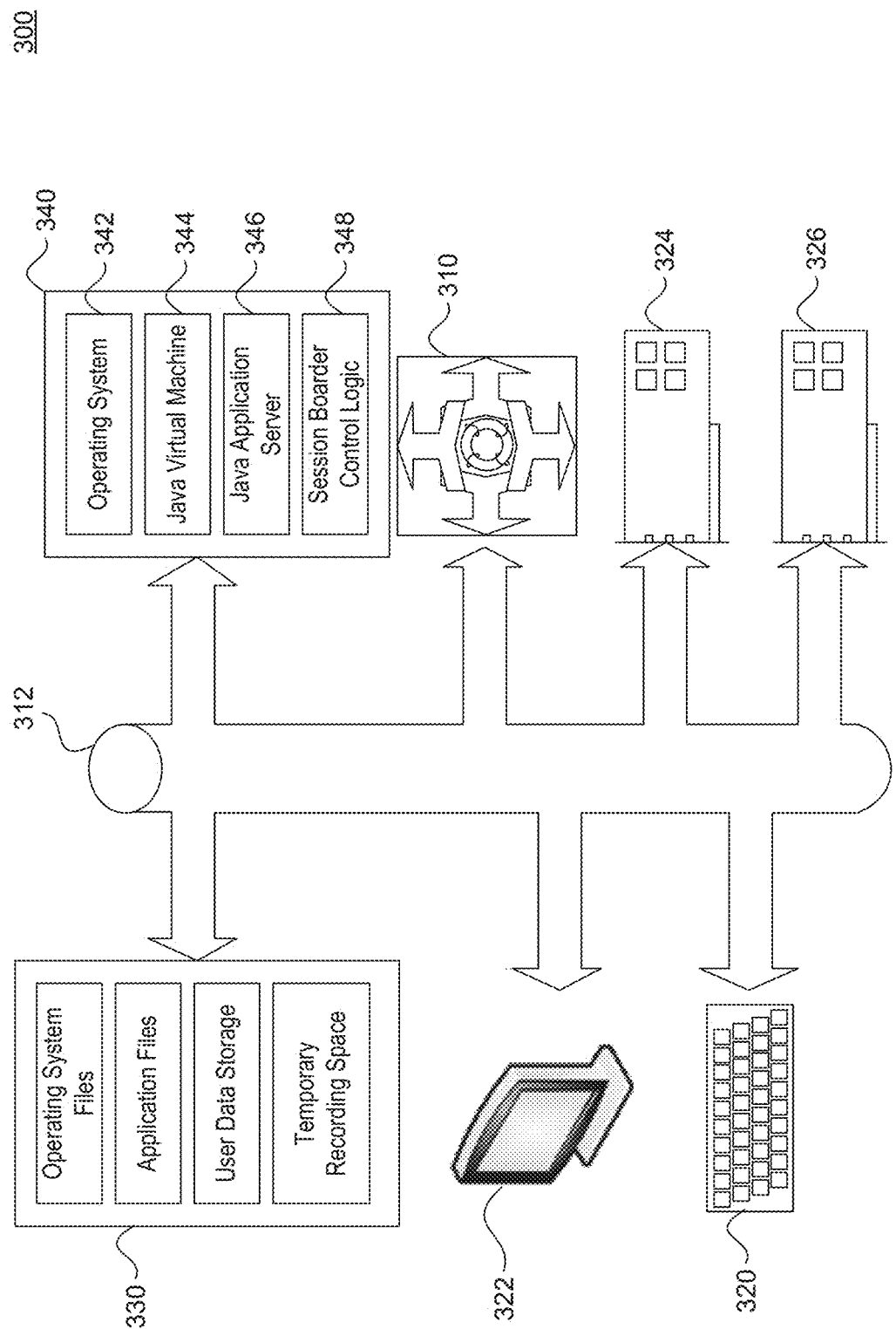
FIG. 3 illustrates a block diagram of a telemedicine server, according to exemplary embodiments of the present disclosure.

FIG. 3 illustrates a block diagram of a telemedicine server 300, according to exemplary embodiments of the present disclosure. The telemedicine server 300 may represent an exemplary embodiment of the telemedicine server 208 depicted in FIG. 2. The telemedicine server 300 functions as the primary logic processing center in the telemedicine system 100. The telemedicine server 300 includes one or more central processing units (CPU) 310 connected via a bus 312 to several other peripherals. Such peripherals include an input device, such as a keyboard and/or mouse 320, a monitor 322 for displaying information, a network interface card 324 and/or a modem 326 that provide network connectivity and communication.

The telemedicine server 300 also includes internal data storage 330. The data storage 330 is non-volatile storage, such as one or more magnetic hard disk drives (HDDs) and/or one or more solid state drives (SSDs). The data storage 330 is used to store a variety of important files, documents, or other digital information, such as the operating system files, application files, user data, and/or temporary recording space.

The telemedicine server 300 also includes system memory 340. The system memory 340 is preferably faster and efficient than the data storage 330, and is configured as random access memory (RAM) in an embodiment. The system memory 340 contains the runtime environment of the application server, storing temporary data for any of the operating system 342, java virtual machine 344, java application server 346, and telemedicine control logic 348.

Medical Center

Figure 4:
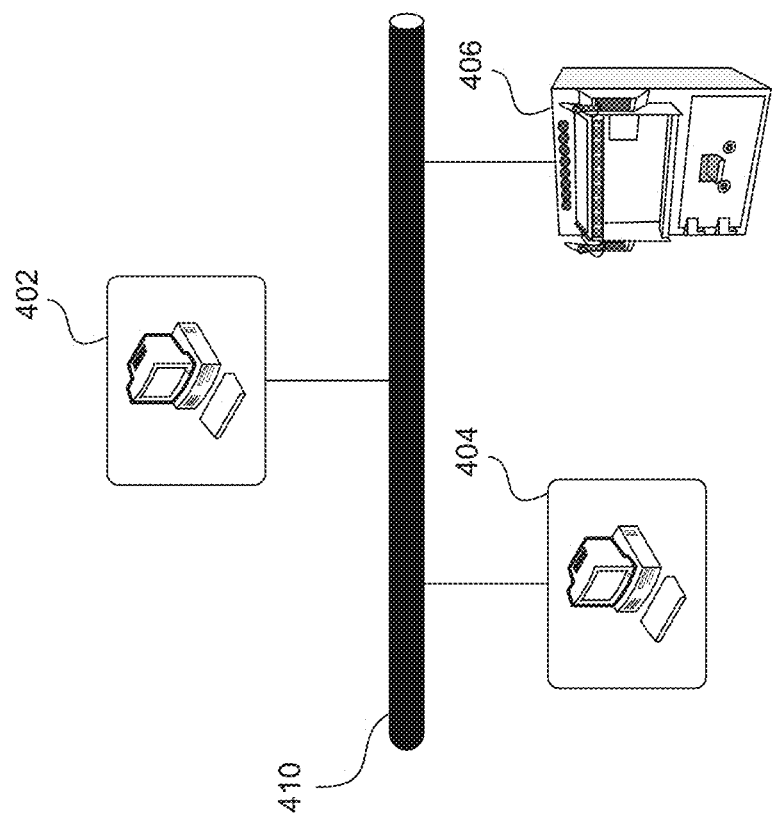
FIG. 4 illustrates a block diagram of a medical center, according to exemplary embodiments of the present disclosure.

FIG. 4 illustrates a block diagram of a medical center 400, according to exemplary embodiments of the present disclosure. The medical center 400 may be an exemplary embodiment of one of the medical centers 142a-142y of FIG. 1. The medical center 400 includes an medical assistant station 402, an inmate station 404, and a medication dispenser 406, that are all connected to each other via a network bus 410.

The medical assistant station 402 is configured to function as a data reviewing center for any local medical assistants stationed at a correctional facility. The medical assistant station 402 may include a computer, tablet, or phone capable of viewing medical data. By way of the medical assistant station 402, a medical assistant may access inmate data such as the medical data from the medical server 204, the billing data from the billing server 206, and/or the scheduling and tracking data from the telemedicine server 208. The medical assistant station 402 includes a medical assistant verification device configured to verify an identity of a medical assistant. Verification of a medical assistant's identity is performed by use of one or more of logon information such as a password verification, a keycard verification, or biometric verification such as voice recognition, retinal recognition, facial recognition, and/or 3D facial architectural recognition. The medical assistant station 402 also includes a medication scanner such as a barcode reader or an RFID reader for scanning medication packets received from the medication center 140.

The inmate station 404 is configured to function as a data reviewing center for an inmate at a correctional facility. The inmate station 404 may include a computer, tablet, or phone capable of viewing medical data. By way of the inmate station 404, an inmate may have access to his/her medical data such as the medical data from the medical server 204, the billing data from the billing server 206, and/or the scheduling and tracking data from the telemedicine server 208. The inmate station 404 includes an inmate verification device configured to verify an identity of an inmate. Verification of an inmate's identity is performed by use of one or more of of logon information such as a password verification, a keycard verification, or biometric verification such as voice recognition, retinal recognition, facial recognition, and/or 3D facial architectural recognition.

The medication dispensing station 406 includes a device configured to receive medication and, after verifications are performed, to dispense the medication through a retrieval bin or other retrieval apparatus. The medication dispensing station 406 may be a standalone device, meaning that all identity verifications are performed remote to the medication dispensing station 406, or, as described in detail below, may be integrated with a verification station(s) such as the inmate station 404.

Figure 5:
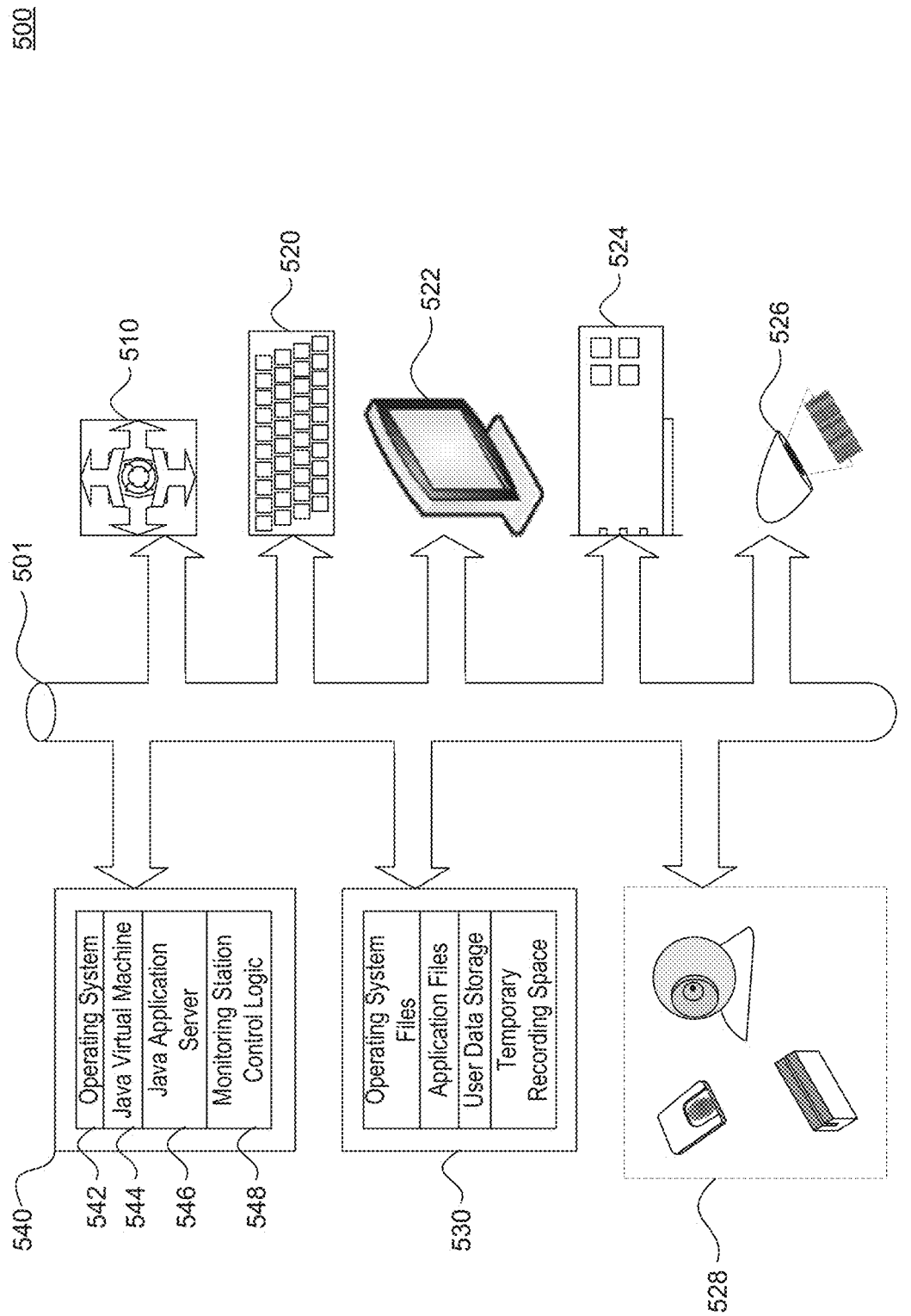
FIG. 5 illustrates a block diagram of a medication dispenser, according to exemplary embodiments of the present disclosure.

FIG. 5 illustrates a block diagram of a medication dispensing station 500, according to exemplary embodiments of the present disclosure. The medication dispensing station 500 may represent an exemplary embodiment of the electrical components of the medication dispensing station 406 depicted in FIG. 4. The medication dispensing station 500 includes one or more central processing units (CPU) 510 connected via a bus 501 to several other peripherals. Such peripherals include an input device, such as a keyboard and/or mouse 520, a monitor 522 for displaying information, a network interface card and/or modem 524 that provide network connectivity and communication with the medical center 400, a medication scanner 526 such as a barcode reader or an RFID reader for scanning medication. The medication scanner 526 can be incorporated internally within a medication dispensing device such that when medication is loaded, or prior to being dispensed, the medication is scanned for verification purposes. In an embodiment, the medication scanner 526 can be externally attached to the medication dispensing device so as to facilitate a medical assistant in scanning medication when loaded or dispensed. Peripherals for the medication dispensing station 500 further include an identification verification device 528 to verify an identity of a medical assistant and/or an inmate. The identification verification device 528 includes one or more of a keycard scanner or a biometric scanner for performing voice recognition, retinal recognition, facial recognition, and/or 3D facial architectural recognition The medication dispensing station 500 also includes internal data storage 530. The data storage 530 is non-volatile storage, such as one or more magnetic hard disk drives (HDDs) and/or one or more solid state drives (SSDs). The data storage 530 is used to store a variety of important files, documents, or other digital information, such as the operating system files, application files, user data, and/or temporary recording space.

The medication dispensing station 500 further includes system memory 540. The system memory 540 is preferably faster and efficient than the data storage 530, and is configured as random access memory (RAM) in an embodiment. The system memory 540 contains the runtime environment of the application server, storing temporary data for any of the operating system 542, java virtual machine 544, java application server 546, and dispenser control logic 548.

Figure 6:
FIG. 6 illustrates a medication label used by the medication dispenser of FIG. 5, according to exemplary embodiments of the present disclosure.

FIG. 6 illustrates a medication label 600 used for identification of medication by the medication dispenser 500, according to exemplary embodiments of the present disclosure. The medication label 600 includes a scannable code, such as the barcode 602, the matrix code 604, a magnetic code and/or an radio frequency identification tag (not shown) that is scannable by the medication scanner 526. The scannable code may contain identifying data for the medication including the type of medication, data of preparation and expiration, location and identity of medication center that distributed the medication, and the inmate to whom the medication is for. As shown by FIG. 6, the medication label 600 may also include identifying data on the label itself.

Figure 7:
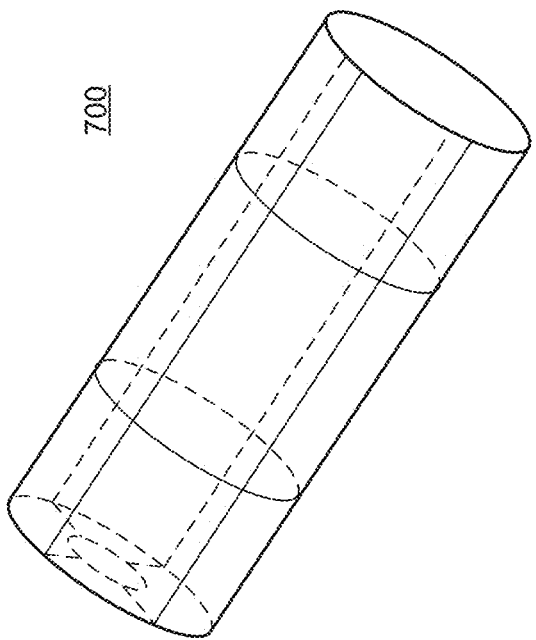
FIG. 7 illustrates a medication canister used by the medication dispenser of FIG. 5, according to exemplary embodiments of the present disclosure.

FIG. 7 illustrates a medication canister 700 used by the medication dispenser 500, according to exemplary embodiments of the present disclosure. The medication canister 700 is manufactured to fit into input slots on the medication dispenser 500 and be dispensed to a retrieval bin of the medication dispenser 500. Further, the medication canister 700 may be manufactured of material that is clear and durable such that the medication label 600 can be scanned by the medication dispenser 500.

Telemedicine System Operation

Operations of the telemedicine system 100 will be described with respect to FIGS. 8 and 9. Although the physical devices and components that form the operations have largely already been described, additional details regarding their more nuanced operation will be described below with respect to FIGS. 1-7. While FIGS. 8 and 9 contain methods of operation of the telemedicine system 100, the operations are not limited to the order described below, and various operations can be performed in a different order. Further, two or more operations of each method may be performed simultaneously with each other.

Figure 8:
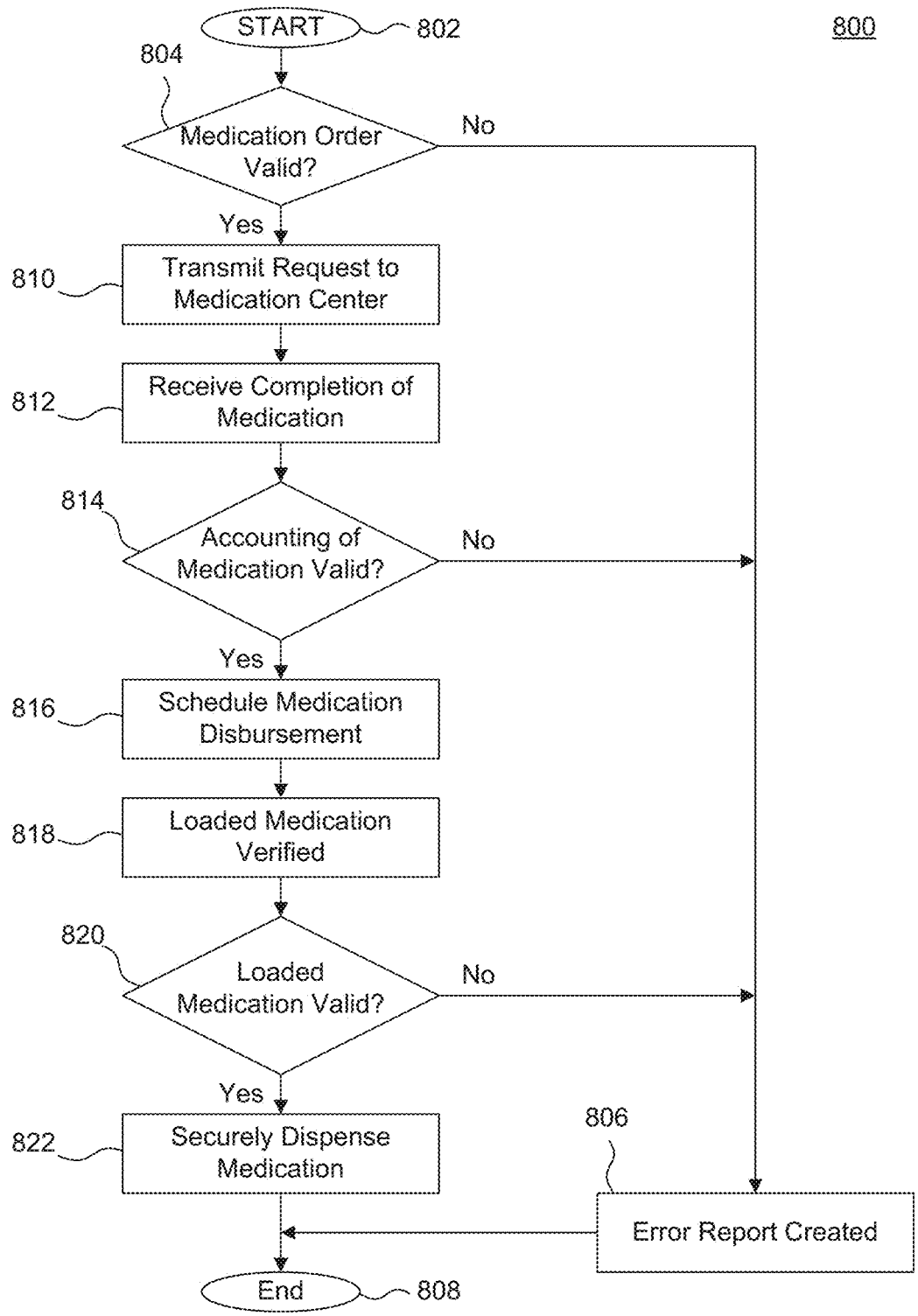
FIG. 8 illustrates a flowchart diagram of a method 800 for securely disbursing medication, according to exemplary embodiments of the present disclosure.

FIG. 8 illustrates a flowchart diagram of a method 800 for securely disbursing medication, according to exemplary embodiments of the present disclosure. When a medication order from a physician center 120 is received, a disbursement process begins (802). For example, the telemedicine center 110 can receive a prescription order from the physician center 120 to begin the disbursement process (802). After the disbursement process begins, the medication order is verified and determined to be valid or not (804). To determine the validity of the medication order, the telemedicine server 110 obtains data such as one or more of a signature of a physician, contact information of a sender of the medication order, or data related to a device that transmitted the medication order, and compares the obtained data to identity data stored in the identity data stored by the identity server 202, to provide some examples. If the medication order is not valid, then an error report is generated (806) by the telemedicine center 120 to report to a correctional facility that the medication order is invalid, and the disbursement process ends (808). If the medication order is valid, the medication order is then transmitted to a medication center 140 (810) for preparation of the medication. For example, the telemedicine center 110 can transmit the medication order to a pharmacy. In another example, the physician center 120 can transmit the medication order to the medication center 140 after receiving a confirmation of the medication order from the telemedicine server 110. In yet another example, the physician center 120 can transmit the medication order simultaneously to telemedicine center 110 and the medication center 140.

A completion message notifying that the medication order has been completed is received (812) after the medication from the medication order has been prepared and shipped. As an example, the telemedicine center 110 can receive from the medication center 140 a message that the medication has been prepared and shipped to the correctional facility. The message may be in the form of a shipping receipt that includes a detailed list of the medication being delivered from the medication center 140. For example, the shipping receipt may include a list of the amount of medication packets being shipped and identify the type of medication in each medication packet. Once the medication has been received, medication packets are scanned at a medical assistant station 402 and a full accounting of the medication is performed (814). An accounting of medication is performed by comparing the scanned medication packets with at least one of the completion message from the medical center 140 or the medication order, to provide an example. If a full accounting is not valid, an error report is generated (806), and the disbursement process ends (808). However, if the accounting is valid, the medication packets are scheduled for disbursement (816). For example, the telemedicine server 208 generates a distribution schedule for a local medical assistant to know when to load medication packets in the medication dispenser 406. The distribution schedule is generated based on medical data, stored by the medical server 204, of a corresponding inmate for whom the medication packets are for and based on a general distribution schedule of the medication dispenser 406. Based on the distribution schedule, medication can then be loaded in a medication canister 700 and the loaded medication canister 700 can be loaded into the medication dispenser 406 by a local medical assistant. Once a medication canister 700 containing a medication packet is loaded into the medication dispenser 406, the medication is scanned by the medication dispenser 406 and verified. The medication dispenser 406 can either perform the verification itself by comparing data from the scanned medication packets against the distribution schedule or by transmitting the data to the telemedicine center 110 for the telemedicine server 208 to compare against the distribution schedule. If the correct medication is not loaded in the medication dispenser 406, an error report is generated (806), and the disbursement process ends (808). Otherwise, the medication stored in the medication dispenser 406 until being securely dispensed (822), and the disbursement process ends (808).

Figure 9:
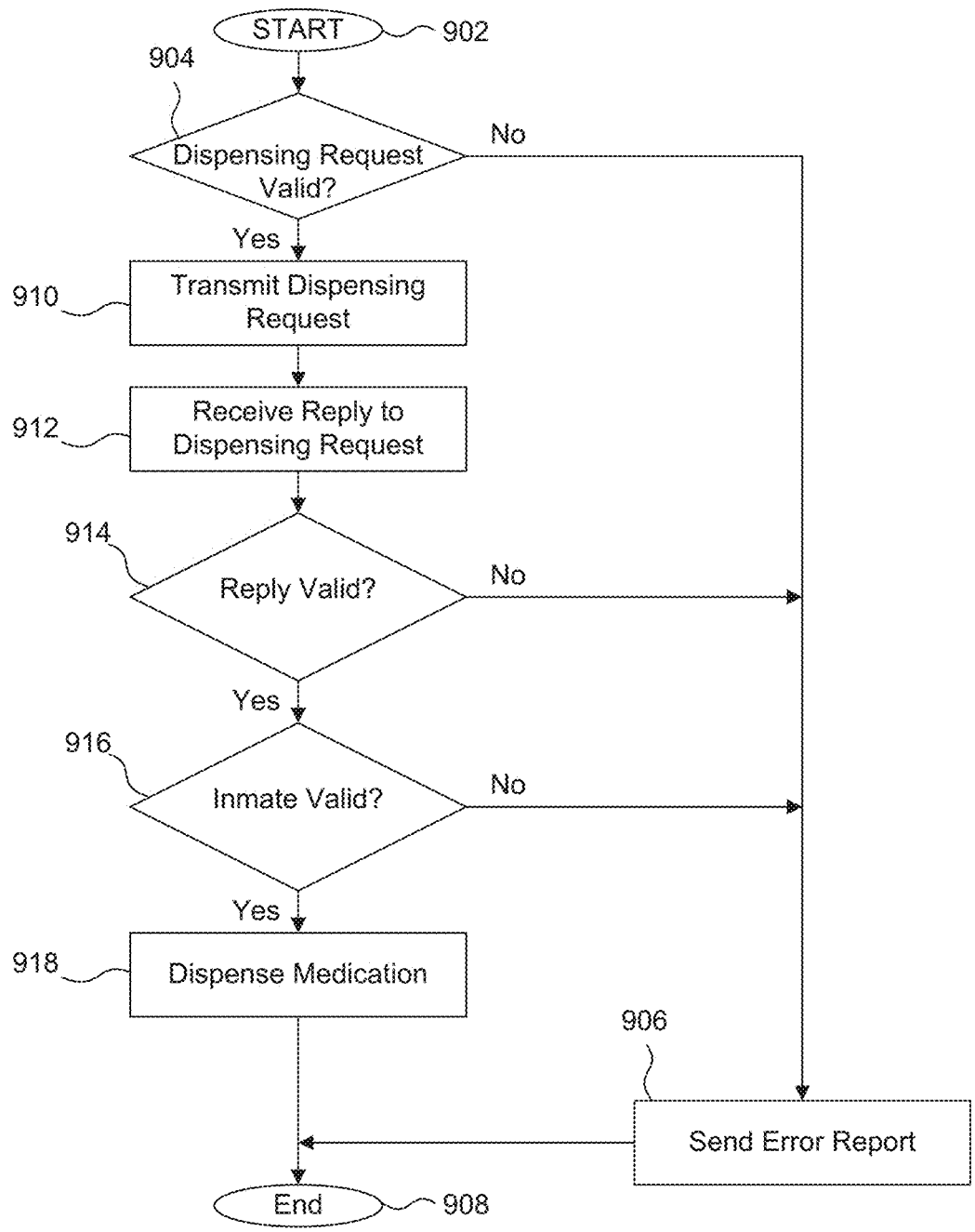
FIG. 9 illustrates a flowchart diagram of a method for securely dispensing medication, according to exemplary embodiments of the present disclosure.

FIG. 9 illustrates a flowchart diagram of a method 900 for securely dispensing medication, according to exemplary embodiments of the present disclosure. The method 900 may represent an exemplary embodiment of the dispensing medication 822 depicted in FIG. 8.

When a first dispensing request is received, a dispensing process starts (902). The first dispensing request is a request from the local medical assistant to have medication dispensed from the medication dispenser 406. The first dispensing request includes data medication data and inmate identity data and data from the medical assistant verification device. The first dispensing request is transmitted by the medical assistant station 402 to the telemedicine center 110. After the first dispensing request is received, the telemedicine center 110 validates the first dispensing request (904). Validation of the first dispensing request is performed by the telemedicine server 208 comparing data from the medical assistant verification device of the medical assistant station 402, received with the first dispensing request, with identity data stored by the identity server 202. If the dispensing request is not valid, meaning the identity of the local medical assistant is not validated, an error report is generated which notifies both the medical assistant station 402 and the medication dispensing station 406 that no medication will be dispensed (906), and the dispensing process ends (908). Otherwise, the telemedicine center 110 transmits a second dispensing request to a physician center 120 (910) to request for approval of dispensing of the medication. The second dispensing request is a request from the telemedicine center 110 to the physician center 120 to have medication dispensed. The second dispensing request includes data regarding the medication to be dispensed and inmate data. In addition, the second dispensing request may include additional data such as data regarding the inmate's medication history. The telemedicine center 110 then receives a reply to the second dispensing request (912) from the physician center 120. At this point, the telemedicine center 110 determines the validity of the reply. To determine the validity of the reply, the telemedicine server 110 verifies one or more of a signature of a physician, contact information of a sender of the reply, or data related to a device that transmitted the reply. For example, the telemedicine server 208 receives the reply and compares the signature of an authorizing physician and the model number of the transmitting device against identity data stored by the identity server 202. If the approval or the validity of the approval are not valid, an error report is generated (906), and the dispensing process ends (908). Otherwise, telemedicine center 110 transmits instructions to the medication dispensing station 406 to dispense the medication. The medication dispensing station 406 receives the instructions and awaits for an inmate validation to be performed (916). The inmate validation is performed when an inmate uses the identification verification device at the medication dispensing station 406. The medication dispensing station 406 can compare data from the identification verification device with identity data from the identity server 202 and data on the medication packets to verify that the inmate at the medication dispensing station 406 is receiving the correct medication. If the inmate validation fails, an error report is generated (906), and the dispensing process ends (908). If the inmate validation passes, the medication dispenser 406 scans the medication through the canister 700 and drops the canister 700 to the delivery bin for an inmate or a medical assistant to retrieve the medication.

Exemplary Computer Implementation

It will be apparent to persons skilled in the relevant art(s) that various elements and features of the present disclosure, as described herein, can be implemented in hardware using analog and/or digital circuits, in software, through the execution of computer instructions by one or more general purpose or special-purpose processors, or as a combination of hardware and software.

Figure 10:
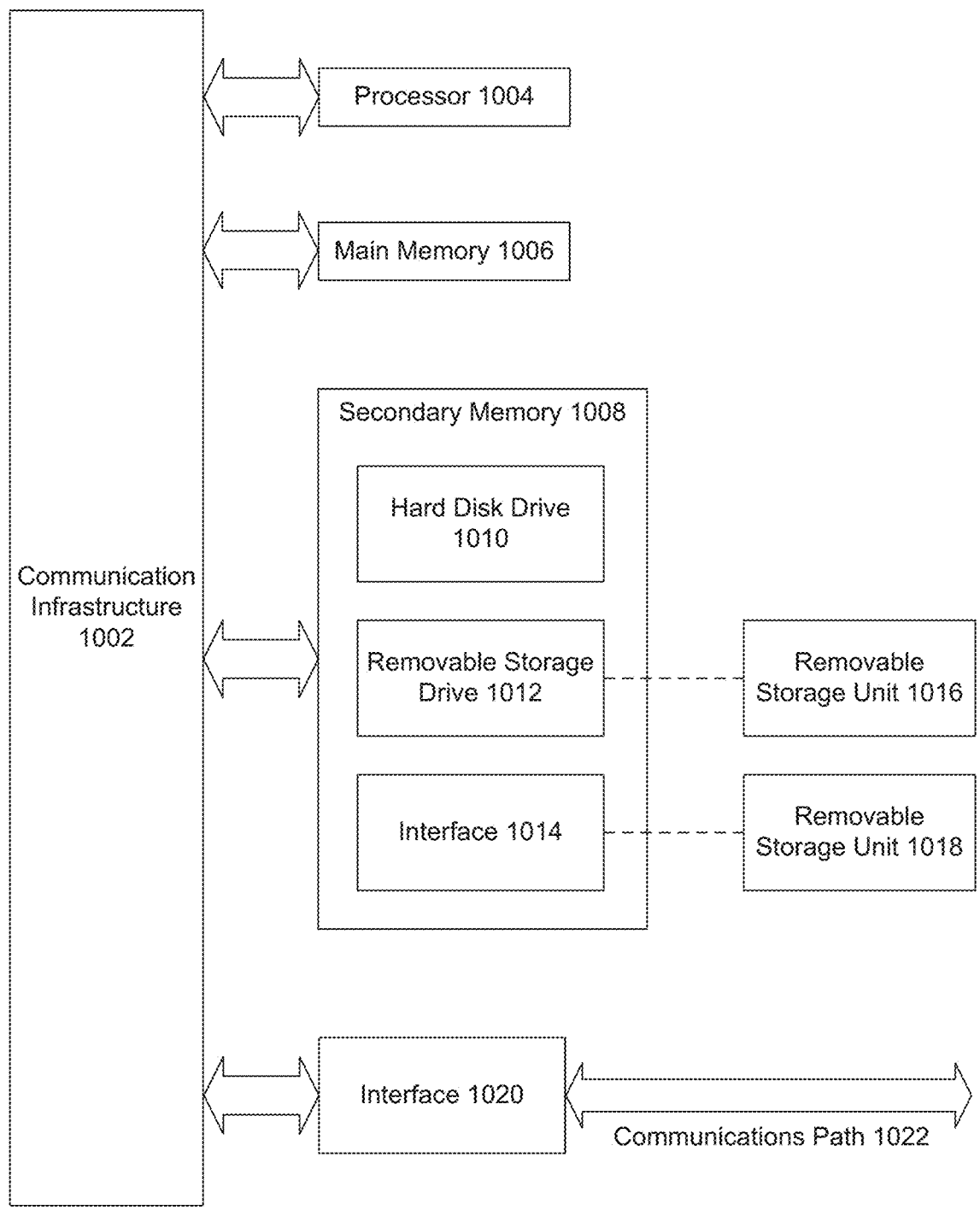
FIG. 10 illustrates a computer system, according to exemplary embodiments of the present disclosure.

The following description of a general purpose computer system is provided for the sake of completeness. Embodiments of the present disclosure can be implemented in hardware, or as a combination of software and hardware. Consequently, embodiments of the disclosure may be implemented in the environment of a computer system or other processing system. For example, the methods of FIGS. 8 and 9 can be implemented in the environment of one or more computer systems or other processing systems. An example of such a computer system 1000 is shown in FIG. 10. One or more of the modules depicted in the previous figures can be at least partially implemented on one or more distinct computer systems 1000.

Computer system 1000 includes one or more processors, such as processor 1004. Processor 1004 can be a special purpose or a general purpose digital signal processor. Processor 1004 is connected to a communication infrastructure 1002 (for example, a bus or network). Various software implementations are described in terms of this exemplary computer system. After reading this description, it will become apparent to a person skilled in the relevant art(s) how to implement the disclosure using other computer systems and/or computer architectures.

Computer system 1000 also includes a main memory 1006, preferably random access memory (RAM), and may also include a secondary memory 1008. Secondary memory 1008 may include, for example, a hard disk drive 1010 and/or a removable storage drive 1012, representing a floppy disk drive, a magnetic tape drive, an optical disk drive, or the like. Removable storage drive 1012 reads from and/or writes to a removable storage unit 1016 in a well-known manner. Removable storage unit 1016 represents a floppy disk, magnetic tape, optical disk, or the like, which is read by and written to by removable storage drive 1012. As will be appreciated by persons skilled in the relevant art(s), removable storage unit 1016 includes a computer usable storage medium having stored therein computer software and/or data.

In alternative implementations, secondary memory 1008 may include other similar means for allowing computer programs or other instructions to be loaded into computer system 1000. Such means may include, for example, a removable storage unit 1018 and an interface 1014. Examples of such means may include a program cartridge and cartridge interface (such as that found in video game devices), a removable memory chip (such as an EPROM, or PROM) and associated socket, a thumb drive and USB port, and other removable storage units 1018 and interfaces 1014 which allow software and data to be transferred from removable storage unit 1018 to computer system 1000.

Computer system 1000 may also include a communications interface 1020. Communications interface 1020 allows software and data to be transferred between computer system 1000 and external devices. Examples of communications interface 1020 may include a modem, a network interface (such as an Ethernet card), a communications port, a PCMCIA slot and card, etc. Software and data transferred via communications interface 1020 are in the form of signals which may be electronic, electromagnetic, optical, or other signals capable of being received by communications interface 1020. These signals are provided to communications interface 1020 via a communications path 1022. Communications path 1022 carries signals and may be implemented using wire or cable, fiber optics, a phone line, a cellular phone link, an RF link and other communications channels.

As used herein, the terms "computer program medium" and "computer readable medium" are used to generally refer to tangible storage media such as removable storage units 1016 and 1018 or a hard disk installed in hard disk drive 1010. These computer program products are means for providing software to computer system 1000.

Computer programs (also called computer control logic) are stored in main memory 1006 and/or secondary memory 1008. Computer programs may also be received via communications interface 1020. Such computer programs, when executed, enable the computer system 1000 to implement the present disclosure as discussed herein. In particular, the computer programs, when executed, enable processor 1004 to implement the processes of the present disclosure, such as any of the methods described herein. Accordingly, such computer programs represent controllers of the computer system 1000. Where the disclosure is implemented using software, the software may be stored in a computer program product and loaded into computer system 1000 using removable storage drive 1012, interface 1014, or communications interface 1020.

In another embodiment, features of the disclosure are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

CONCLUSION

It is to be appreciated that the Detailed Description section, and not the Abstract section, is intended to be used to interpret the claims. The Abstract section may set forth one or more, but not all exemplary embodiments, and thus, is not intended to limit the disclosure and the appended claims in any way.

The invention has been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

It will be apparent to those skilled in the relevant art(s) that various changes in form and detail can be made therein without departing from the spirit and scope of the disclosure. Thus, the invention should not be limited by any of the above-described exemplary embodiments, but should be defined only in accordance with the following claims and their equivalents.

What is claimed is:

1. A telemedicine system for a correctional facility, comprising:
a telemedicine center comprising a plurality of databases storing identity data and medical data;
a telemedicine server, connected to the telemedicine center and a medication dispensing station via a network, wherein the telemedicine server is configured to:
receive, from a physician center located remote to the correctional facility, a medication order for an inmate at the correctional facility;
verify the medication order by comparing data associated with the medication order with the identity data stored in plurality of databases, wherein the verifying includes comparing a model number of a transmitting device at the physician center with identity data of physicians at the physician center, the identity data of the physicians including a model number of physician devices associated with the physicians;
in response to the verifying, transmit a first dispensing request from a local medical assistant station at the correctional facility to the telemedicine center, wherein the first dispensing request comprises medication data, inmate identity data, and data from a medical assistant verification device;
validate an identity of a local medical assistant using the first dispensing request;
in response to validation of the identity of the local medical assistant, transmit a second dispensing request from the telemedicine center to the physician center, wherein the second dispensing request comprises inmate data and data regarding the medication to be dispensed;
transmit a reply from the physician center to the telemedicine center;
determine a validity of the reply by comparing a signature of an authorizing physician, contact information, and data related to the device that transmitted the reply against identity data stored in an identity server;
in response to successfully validating the reply, transmit instructions from the telemedicine center to the medication dispensing station to dispense the medication; and
receive, from the medication dispensing station, a completion message indicating that one or more medications in the medication order have been prepared and shipped to the correctional facility; and
the medication dispensing station configured to:
scan, using a medication scanner, at least one medication label of the one or more medications received at the correctional facility;
generate a distribution schedule for the one or more medications based on at least one of the identity data and medical data obtained by scanning the at least one medication label;
generate instructions for a medical assistant associated with the medication dispensing station to load the medication in a medication dispensing device according to the distribution schedule;
verify an identity of the inmate using at least one of voice recognition, retinal recognition, facial recognition, and 3D facial architectural recognition; and
dispense the medication to the inmate based on the distribution schedule in response to successfully verifying the identity of the inmate.

2. The telemedicine system of claim 1, wherein the data associated with the medication order comprises one or more of the signature of the authorizing physician at the physician center, contact information of a sender of the medication order, or data related to the device that transmitted the medication order.

3. The telemedicine system of claim 1, wherein the identity data comprises one or more names, biometric data, contact data, and device data of inmates and one or more physicians with access to the telemedicine system.

4. The telemedicine system of claim 1, wherein the completion message comprises an electronic shipping receipt including a list of the one or more medications being shipped, an amount of each medication, and a medication type of each medication.

5. The telemedicine system of claim 1, wherein the medication scanner comprises a barcode reader or a radio frequency identification (RFID) reader configured to scan the at least one medication label of the one or more medications.

6. The telemedicine system of claim 1, wherein the at least one medication label comprises a scannable code identifying a type of each medication, preparation and expiration data of each medication, location and identity of the medication dispensing station, and a name of the inmate associated with each medication.

7. The telemedicine system of claim 1, wherein the medical data comprises medication request data, check-up data, medical questionnaires, billing history, and patient information of a plurality of inmates in the correctional facility.

8. A telemedicine server comprising:
a memory;
a network interface; and
at least one processor coupled to the memory, wherein the telemedicine server is communicatively coupled to a physician center, a local medical assistant station at a correctional facility and a medication dispensing station via the network interface, and wherein the at least one processor is configured to:
receive, from the physician center, a medication order for an inmate at the correctional facility;
verify the medication order by comparing data associated with the medication order with identity data stored in the memory, wherein the verifying includes comparing a model number of a transmitting device at the physician center with identity data of physicians at the physician center, the identity data of the physicians including a model number of physician devices associated with the physicians;
transmit a first dispensing request from the local medical assistant station to the telemedicine server, wherein the first dispensing request comprises medication data, inmate identity data, and data from a medical assistant verification device;
validate an identity of a local medical assistant using the first dispensing request;
in response to validation of the identity of the local medical assistant, transmit a second dispensing request from the telemedicine server to the physician center, wherein the second dispensing request comprises inmate data and data regarding the medication to be dispensed;

transmit a reply from the physician center to the telemedicine server;

determine a validity of the reply by comparing a signature of an authorizing physician, contact information, and data related to a device that transmitted the reply against identity data stored in an identity server;

in response to successfully validating the reply, transmit instructions from the telemedicine server to the medication dispensing station to dispense the medication;

in response to the verifying, transmit the medication order to the medication dispensing station;

generate instructions for a medical assistant associated with the medication dispensing station to load the medication in a medication dispensing device according to a distribution schedule;

verify an identity of the inmate using at least one of voice recognition, retinal recognition, facial recognition, and 3D facial architectural recognition; and receive, from the medication dispensing station, a completion message indicating that one or more medications in the medication order have been prepared and shipped to the correctional facility, wherein the one or more medications are scanned using a medication scanner at a medication dispensing station in the correctional facility after delivery of the one or more medications to the correctional facility and dispensed to the inmate based on the distribution schedule generated by the scanning.

9. The telemedicine server of claim 8, wherein the data associated with the medication order comprises one or more of the signature of the authorizing physician, contact information of a sender of the medication order, or data related to a device that transmitted the medication order.

10. The telemedicine server of claim 8, wherein the identity data comprises one or more names, biometric data, contact data, and device data of inmates and one or more physicians with access to the telemedicine server.

11. The telemedicine server of claim 8, wherein the completion message comprises an electronic shipping receipt including a list of the one or more medications being shipped, an amount of each medication, and a medication type of each medication.

12. The telemedicine server of claim 8, wherein the one or more medications include a scannable code identifying a type of each medication, preparation and expiration data of each medication, location and identity of the medication dispensing station, and a name of the inmate associated with each medication.

13. The telemedicine server of claim 12, wherein the scannable code comprises a barcode, a matrix code, a magnetic code, or a radio frequency identification (RFID) tag.

14. A method for securely dispensing medication at a correctional facility, the method comprising:

receiving, from a physician center located remote to the correctional facility, by at least one processor of a telemedicine server for the correctional facility, a medication order for an inmate at the correctional facility, wherein the physician center is connected to the telemedicine server via a network;

verifying, by the at least one processor, the medication order by comparing data associated with the medication order with identity data stored in a plurality of databases associated with the telemedicine server, wherein the verifying comprises comparing a model number of a transmitting device at the physician center with identity data of physicians at the physician center, the identity data of the physicians including a model number of physician devices associated with the physicians;

in response to the verifying, transmitting a first dispensing request from a local medical assistant station at the correctional facility to a telemedicine center, wherein the first dispensing request comprises medication data, inmate identity data, and data from a medical assistant verification device;

validating, by the telemedicine server, an identity of a local medical assistant using the first dispensing request;

in response to validation of the identity of the local medical assistant, transmitting a second dispensing request from the telemedicine center to the physician center, wherein the second dispensing request comprises inmate data and data regarding the medication to be dispensed;

transmitting a reply from the physician center to the telemedicine center;

determining a validity of the reply by comparing a signature of an authorizing physician, contact information, and data related to a device that transmitted the reply against identity data stored in an identity server;

in response to successfully validating the reply, transmitting instructions from the telemedicine center to the medication dispensing station to dispense the medication;

receiving, from the medication dispensing station, a completion message indicating that one or more medications in the medication order have been prepared and shipped to the correctional facility, wherein the one or more medications are scanned using a medication scanner after delivery of the one or more medications to the correctional facility;

generating instructions for a medical assistant associated with the medication dispensing station to load the medication in a medication dispensing device according to a distribution schedule;

verifying an identity of the inmate using at least one of voice recognition, retinal recognition, facial recognition, and 3D facial architectural recognition; and generating, by the at least one processor, the distribution schedule for the one or more medications based on at least one of the identity data and medical data obtained by scanning the one or more medications, wherein the medication is dispensed to the inmate based on the distribution schedule.

15. The method of claim 14, wherein the data associated with the medication order comprises one or more of the signature of the authorizing physician, contact information of a sender of the medication order, or data related to a device that transmitted the medication order.

16. The method of claim 14, wherein the identity data comprises one or more names, biometric data, contact data, and device data of inmates and one or more physicians with access to the telemedicine server.

17. The method of claim 14, wherein the completion message comprises an electronic shipping receipt including a list of the one or more medications being shipped, an amount of each medication, and a medication type of each medication.

18. The method of claim 14, wherein the one or more medications include a scannable code identifying a type of each medication, preparation and expiration data of each medication, location and identity of the medication dispensing station, and a name of the inmate associated with each medication.

19. The method of claim 18, wherein the scannable code comprises a barcode, a matrix code, a magnetic code, or a radio frequency identification (RFID) tag.

20. The method of claim 14, wherein the medical data comprises medication request data, check-up data, medical questionnaires, billing history, and patient information of a plurality of inmates in the correctional facility.

\* \* \* \* \*

UNITED STATES PATENT AND TRADEMARK OFFICE
CERTIFICATE OF CORRECTION

PATENT NO. : 11,948,218 B2
APPLICATION NO. : 17/228195
DATED : April 2, 2024
INVENTOR(S) : Hodge It is certified that error appears in the above-identified patent and that said Letters Patent is hereby corrected as shown below:

In the Specification

In Column 4, Line 6, delete "devises" and insert -- devices --, therefor.

In Column 6, Line 23, delete "assist" and insert -- assistant --, therefor.

In Column 7, Line 48, delete "of of" and insert -- of --, therefor.

In the Claims

In Column 14, Claim 2, Line 6, after "physician" delete "at the physician center".

Signed and Sealed this
Tenth Day of December, 2024

*Katherine Kelly Vidal*

Katherine Kelly Vidal
*Director of the United States Patent and Trademark Office*